United States Patent [19]
Rogozinski

[11] Patent Number: 5,573,286
[45] Date of Patent: Nov. 12, 1996

[54] KNOT

[76] Inventor: Chaim Rogozinski, 3223 Front Rd., Jacksonville, Fla. 32217

[21] Appl. No.: 405,011
[22] Filed: Mar. 15, 1995
[51] Int. Cl.⁶ .............................. D04G 5/00; B65H 69/04
[52] U.S. Cl. .............................. 289/12; 289/1.5; 606/228
[58] Field of Search .............................. 289/1.2, 1.5, 17, 289/18.1; 606/139, 144, 148, 228

[56] References Cited

PUBLICATIONS

The Encyclopedia of Knots and Fancy Rope Work, Graumont and Henzel, Pub. 1945, pp. 11–24 and 86–89.

Primary Examiner—Michael A. Neas
Attorney, Agent, or Firm—Edward S. Irons

[57] ABSTRACT

A knot formed by providing a bight in a strand, then forming a lark's head in the bight so as to produce a pair of adjacent loops and a pair of free ends extending from the loops, then passing the free ends around the object and passing them through both said loops in series, and then tying at least one overhand hitch in the free ends to resist any forces tending to pull the free ends back through the loops.

The knot is useful in orthopedic surgical procedures.

11 Claims, 2 Drawing Sheets

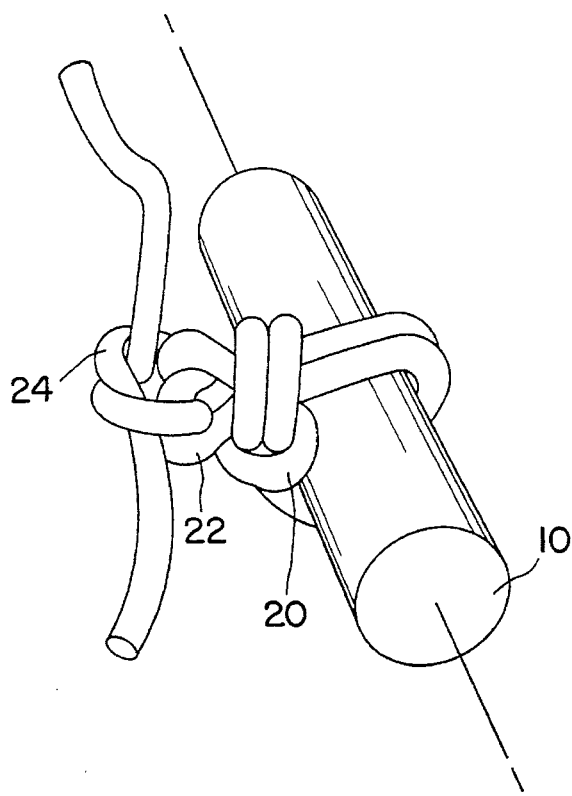
FIG. 1
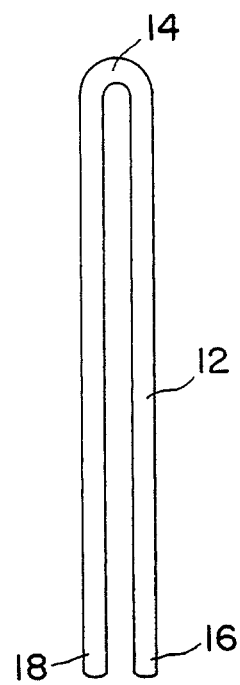
FIG. 2
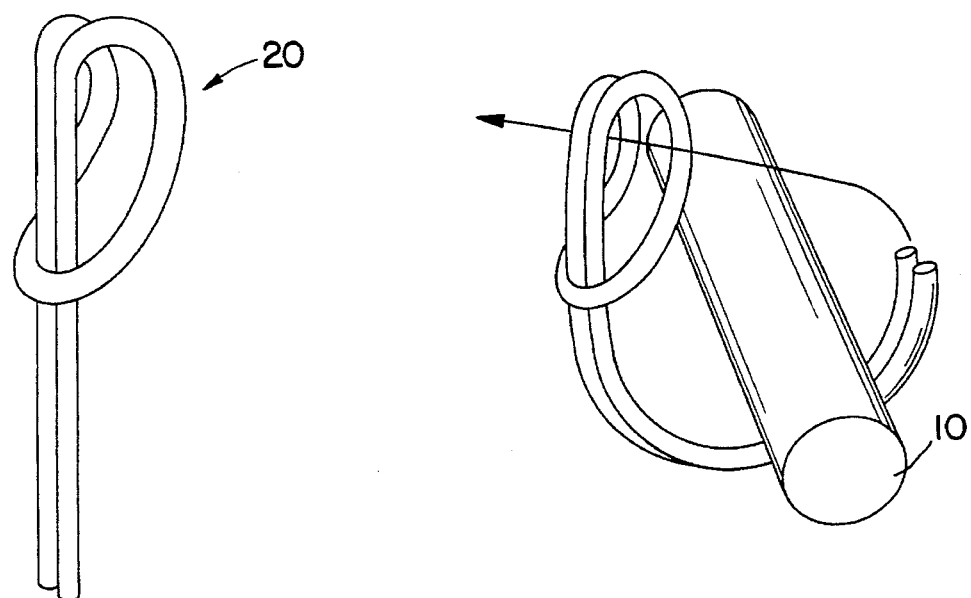
FIG. 3
FIG. 4

KNOT

FIELD OF INVENTION

This invention relates to a knot and a method for forming it. More particularly, the invention relates to a knot for use in orthopedic surgical techniques.

BACKGROUND OF THE INVENTION

Orthopedic and other surgical techniques require the use of ligature knots as the operation proceeds. Metallic ligatures must be cut to length with consequent sharp ends.

Known surgical knots are difficult to form, particularly in the course of the procedure. This problem has motivated the production of factory pre-tied knots which tend to be expensive.

There is accordingly a need for a knot which can easily be formed by the surgeon from a ligature material saleable in spools. There is also a need for such a knot which can be progressively tightened to achieve and which will thereafter maintain a desired tension and which permits doubling of ligature strands.

SUMMARY OF THE INVENTION

This invention provides a knot which may readily be formed with double strands of a non-metallic ligature material as surgery proceeds.

The knot can be tightened progressively to attain and thereafter maintain a desired tension prior to the forming of a final security locking knot such as a half hitch. It is therefore significantly advantageous when used as a cerclage method on long bones or sublaminar fixation in spines.

DETAILED DESCRIPTION OF THE INVENTION

The knot of the invention is tied by first forming a bight in a strand of any desired, preferably non-metallic ligature material and thereafter a lark's head in the bight so as to produce a pair of adjacent loops and a pair of free ends extending from the loops. The free ends are passed around an object and thence through both said loops in series. Preferably, a second knot is tied in at least one of the free ends to resist any forces tending to pull the free ends back through the loops.

BRIEF DESCRIPTION OF THE DRAWINGS

In the accompanying drawings:

FIG. 1 is a perspective view of a complete knot embodying the invention.

FIGS. 2 through 6 are sequential perspective views showing how the knot is tied or formed.

DESCRIPTION OF THE PREFERRED EMBODIMENT

Figure 5:
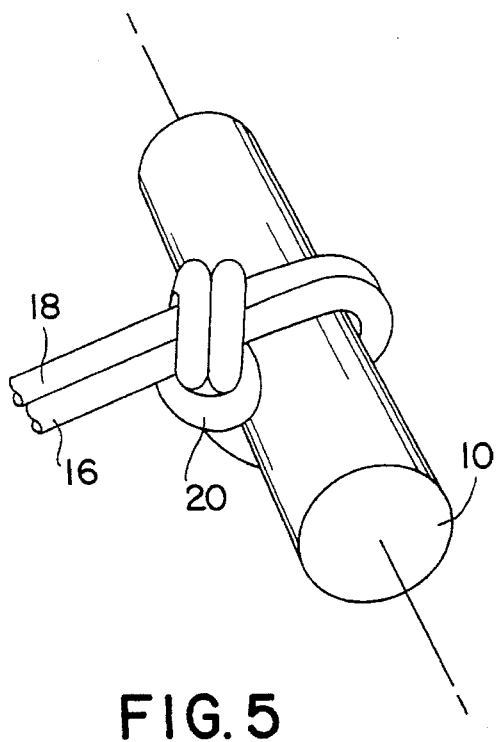
Figure 6:
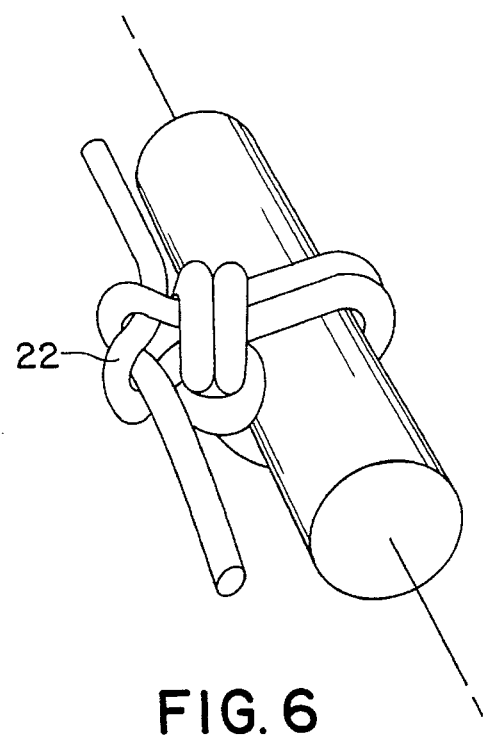

In the accompanying drawings, reference numeral 10 designates an object such as a long bone. A knot according to the invention is tied to an object by the steps illustrated in FIGS. 2 through 6.

First a strand 12 of flexible material such as suturing thread is doubled upon itself (FIG. 2) to form a U-shaped bight 14 at one end. The free ends 16, 18 are now next to one another.

The bight 14 is next folded down against the strands (FIG. 3), to form a so-called "lark's head" 20, which comprises a pair of symmetrical loops adjacent one another.

Now, the free ends of the strand are passed around the object (FIG. 4), and then through both loops of the lark's head (FIG. 5). Pulling on the free ends tightens the knot around the object.

Figure 7:
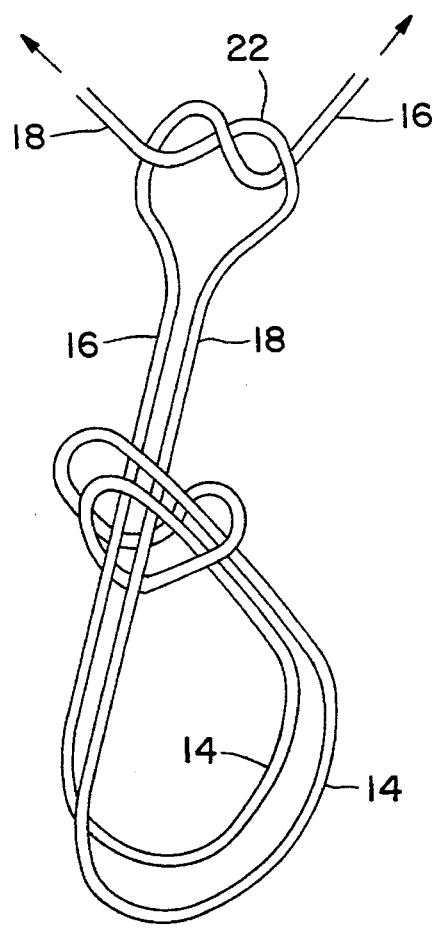
FIG. 7 is a schematic perspective view of the formation of the knot prior to the tightening of the strands.

If desired to hold the knot tension, at least one overhand knot 22, e.g., a half hitch, is tied in the free ends (FIGS. 5, 6 and 7), and drawn down against the knot already formed. Advantageously, the overhand knot can slip, so more tension can be applied as needed, simply by pulling the free ends away from one another. Where the knot is to remain in place long term, an additional overhand knot 24 of opposite hand is applied, creating a more secure square knot. By "opposite hand" is meant that the ends are passed left-over-right in the second knot, if the first was right-over-left.

I claim:

1. A knot comprising strand in the form of a lark's head including two loops and a pair of free ends, both of said free ends passing around an object to be secured by said knot and then through said two loops in series, and a reverse knot formed in at least one of said free ends of said pair to resist forces tending to pull said at least one free end back through said loops.

2. A knot comprising strand in the form of a lark's head including two loops and a pair of free ends, both of said free ends passing around an object to be secured by said knot and then through said two loops in series, and a reverse knot formed in at least one of said free ends of said pair to resist forces tending to pull said at least one free end and a half hitch formed in said pair of free ends.

3. A method of tying a knot, said method comprising the steps of forming a bight in a strand, forming a lark's head in the bight so as to produce a pair of adjacent loops and a pair of free ends extending from the loops, passing the free ends around an object to be secured by said knot thereafter passing said free ends through each of said adjacent loops in series, and thereafter tying a first overhand knot in said free ends, to resist any force tending to pull said at least one free end back through said loops.

4. The method of claim 3, further comprising a last step of tying a second overhand knot in the free ends for added security, and drawing the second overhand knot against the first.

5. The method of claim 4, wherein the second overhand knot is of opposite hand to the first, so that said first and second overhand knots form a square knot.

6. The knot of claim 1 or claim 2 in which said strand is non-metallic.

7. A knot comprising strand in the form of a lark's head including two loops and a pair of free ends, both of said free ends passing around an object to be secured by said knot and then through said two loops in series, and a reverse knot formed in at least one of said free ends of said pair to resist forces tending to pull said at least one free end back through said loops, wherein said knot can be progressively tightened to achieve and maintain a desired tension by pulling said free ends after passage around said object and through said two loops.

8. A knot comprising strand in the form of a lark's head including two loops and a pair of free ends, both of said free ends passing around an object to be secured by said knot and then through said two loops in series, and a reverse knot formed in at least one of said free ends of said pair to resist forces tending to pull said at least one free end and a half hitch formed in said pair of free ends;

wherein said knot can be progressively tightened to achieve and maintain a desired tension by pulling said free ends after passage around said object and through said two loops.

9. A method of tying a knot, said method comprising the steps of forming a bight in a strand, forming a lark's head in the bight so as to produce a pair of adjacent loops and a pair of free ends extending from the loops, passing the free ends around an object to be secured by said knot thereafter passing said free ends through each of said adjacent loops in series, and thereafter tying a first overhand knot in at least one of said free ends, the free ends to resist any force tending to pull said at least one free end back through said loops;

wherein said knot can be progressively tightened to achieve and maintain a desired tension by pulling said free ends after passage around said object and through said two loops.

10. In an orthopedic surgical technique which requires the tying of a ligature knot as the technique proceeds, the improvement which comprises tying said knot by (i) forming a lark's head in a non-metallic ligature said lark's head including two loops and two free ends;

(ii) passing said two free ends around an object to be secured by said knot and then through each of said two loops; and (iii) progressively tightening the knot so formed to achieve a desired tension
wherein said desired tension is maintained as
said surgical technique proceeds, and (iv) thereafter tying at least a first overhand knot in at least one of said free ends to resist any force tending to pull said one free end back through said loops.

11. The orthopedic surgical technique of claim 10 further comprising the step of tying a second overhand knot in said free ends and drawing said second overhand knot against the first.

\* \* \* \* \*